US011771838B2

(12) United States Patent
Helmer et al.

(10) Patent No.: US 11,771,838 B2
(45) Date of Patent: Oct. 3, 2023

(54) AUDIBLE INDICATOR (71) Applicant: Sanofi-Aventis Deutschland GMBH, Frankfurt am Main (DE)

(72) Inventors: Michael Helmer, Frankfurt am Main (DE); Marc Schader, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 741 days.

(21) Appl. No.: 16/328,251

(22) PCT Filed: Aug. 23, 2017

(86) PCT No.: PCT/EP2017/071209
§ 371 (c)(1),
(2) Date: Feb. 25, 2019

(87) PCT Pub. No.: WO2018/037034
PCT Pub. Date: Mar. 1, 2018

(65) Prior Publication Data
US 2021/0275750 A1    Sep. 9, 2021

(30) Foreign Application Priority Data
Aug. 26, 2016  (EP) ..................... 16185803

(51) Int. Cl.
*A61M 5/315*    (2006.01)
*A61M 5/20*    (2006.01)
(52) U.S. Cl.
CPC ........ *A61M 5/3157* (2013.01); *A61M 5/2033* (2013.01); *A61M 2205/581* (2013.01)

(58) Field of Classification Search
CPC .............. A61M 5/3157; A61M 5/2033; A61M 2205/581
See application file for complete search history.

(56) References Cited

U.S. PATENT DOCUMENTS

| 5,090,962 A | 2/1992 | Landry, Jr. et al. |
| 5,127,906 A | 7/1992 | Landry, Jr. et al. |

(Continued)

FOREIGN PATENT DOCUMENTS

| CN | 1089510 | 7/1994 |
| CN | 102209563 | 10/2011 |

(Continued)

OTHER PUBLICATIONS

International Preliminary Report on Patentability in International Application No. PCT/EP2017/071209, dated Feb. 26, 2019, 7 pages.

(Continued)

*Primary Examiner* — James D Ponton
*Assistant Examiner* — Neeraja Gollamudi
(74) *Attorney, Agent, or Firm* — Fish & Richardson P.C.

(57) ABSTRACT

The present disclosure relates to an audible indicator for use with a drug delivery device comprising a resilient force member configured to reside in one of a relaxed state and a biased state. The audible indicator comprises a retainer adapted to maintain the resilient force member in the biased state. The resilient force member releases stored energy to impact a surface to generate an audible signal when the resilient force member changes from the biased state into the relaxed state.

19 Claims, 4 Drawing Sheets

(56) References Cited

U.S. PATENT DOCUMENTS

| | | | |
|---|---|---|---|
| 5,391,157 A | 2/1995 | Harris et al. | |
| 2009/0192443 A1* | 7/2009 | Collins, Jr. | A61M 11/042 604/24 |
| 2009/0287161 A1 | 11/2009 | Traub et al. | |
| 2012/0071837 A1* | 3/2012 | O'Connor | A61M 5/1454 604/232 |

FOREIGN PATENT DOCUMENTS

| | | | |
|---|---|---|---|
| CN | 103492002 | 1/2014 | |
| CN | 104080499 | 10/2014 | |
| EP | 2438940 | 4/2012 | |
| EP | 2489385 | 8/2012 | |
| EP | 2489385 A1 * | 8/2012 | A61M 5/3157 |
| EP | 4026575 | 7/2022 | |
| JP | H02-302266 | 12/1990 | |
| JP | H06-190041 | 7/1994 | |
| JP | 2014-508000 | 4/2014 | |
| KR | 20090049968 | 5/2009 | |
| WO | WO 2010/035059 | 4/2010 | |
| WO | WO 2012/110578 | 8/2012 | |
| WO | WO 2012/117252 | 9/2012 | |
| WO | WO 2013/057033 | 4/2013 | |
| WO | WO 2015/151693 | 10/2015 | |
| WO | WO 2016/001304 | 1/2016 | |
| WO | WO 2016/027096 | 2/2016 | |
| WO | WO 2016/114985 | 7/2016 | |
| WO | WO-2016193344 A1 * | 12/2016 | A61M 5/24 |

OTHER PUBLICATIONS

International Search Report and Written Opinion in International Application No. PCT/EP2017/071209, dated Mar. 11, 2017, 9 pages.

* cited by examiner

FIG 7

AUDIBLE INDICATOR

CROSS REFERENCE TO RELATED APPLICATIONS

The present application is the national stage entry of International Patent Application No. PCT/EP2017/071209, filed on Aug. 23, 2017, and claims priority to Application No. EP 16185803.0, filed on Aug. 26, 2016, the disclosures of which are incorporated herein by reference.

TECHNICAL FIELD

The present disclosure relates to an audible indicator for use with a drug delivery device.

BACKGROUND

Administering an injection is a process, which presents a number of risks and challenges for users and healthcare professionals, both mental and physical. Injection devices typically fall into two categories—manual devices and auto-injectors. In a conventional manual device, manual force is required to drive a medicament through a needle. This is typically done by some form of button/plunger that has to be continuously pressed during the injection.

Autoinjector devices aim to make self-injection easier for patients. A conventional autoinjector may provide the force for administering the injection by a spring, and a trigger button or other mechanism may be used to activate the injection. Autoinjectors may be single-use or reusable devices.

SUMMARY

According to the present disclosure, an audible indicator for use with a drug delivery device comprises a resilient force member configured to reside in one of a relaxed state and a biased state,
wherein the audible indicator comprises a retainer adapted to abut a plunger to maintain the resilient force member in the biased state,
wherein the resilient force member releases stored energy to impact a surface to generate an audible signal when the resilient force member changes from the biased state into the relaxed state.

In the context of the present application, the relaxed state is a state in which the spring element has a relatively low potential energy whereas the biased state is a state in which the spring element has a potential energy, which is higher than in the relaxed state. When the spring element changes from the biased state into the relaxed state, stored energy is released from the spring element.

The audible indicator can be used for indicating an end of dose to a patient or user, i.e. that at least almost the full dose of medicament in the drug delivery device was spent. Thus, the drug delivery device is improved in order to achieve a reliable indication of the end of medicament delivery and a full effectiveness of the medicament within the patient. In mechanically driven drug delivery devices, interacting parts are subject to manufacturing tolerances, so the audible indicator may have to be released before the dose is indeed fully spent.

The resilient force member may change from the biased state into the relaxed state by a movement of a plunger that is used to displace the drug from a medicament container. For example, the resilient force member may change from the biased state into the relaxed state when the plunger moves towards or reaches a distal position at the end of a medicament delivery process.

In an exemplary embodiment, the resilient force member comprises a resilient material, e.g. spring steel or spring plastic.

In an exemplary embodiment, the retainer is provided by a movable support arm adapted to radially inwardly abut the plunger when the plunger is in the proximal position.

In an exemplary embodiment, the resilient force member comprises a center and two legs such that the resilient force member assumes an Ω-shaped, U-shaped or horseshoe-shaped cross section in the biased state.

In an exemplary embodiment, the retainer is arranged as a notch formed in the support arm, adapted to receive the legs in the biased state. Movement of the support arm away from the resilient force member pulls the legs of the resilient force member out of the retainer, i.e. the notch, so the legs relax and move away from each other and strike the surface thereby generating a recognizable audible signal.

In an exemplary embodiment, the resilient force member is a leaf spring having a first end adapted to be fixed and a free second end.

In an exemplary embodiment, the retainer is arranged as a radially outwardly directed beam having a protrusion on the support arm, wherein the second end of the resilient force member is retained by the protrusion when the resilient force member is in the biased state.

According to an aspect of the present disclosure, a drug delivery device comprises a case, a plunger and an audible indicator comprising a resilient force member configured to reside in one of a relaxed state and a biased state,
wherein the audible indicator comprises a retainer adapted to abut the plunger to maintain the resilient force member in the biased state,
wherein the resilient force member releases stored energy to impact a surface of the case to generate an audible signal when the resilient force member changes from the biased state into the relaxed state.

The audible indicator can be used for indicating to a patient or user that the full dose of medicament in the drug delivery device was spent. Thus, the drug delivery device is improved in order to achieve a reliable indication of the end of medicament delivery and a full effectiveness of the medicament within the patient.

The resilient force member may change from the biased state into the relaxed state by a movement of a plunger that is used to displace the drug from a medicament container. For example, the resilient force member may change from the biased state into the relaxed state when the plunger moves towards or reaches a distal position at the end of a medicament delivery process.

In an exemplary embodiment, the retainer is provided by a movable support arm adapted to radially inwardly abut the plunger when the plunger is in a proximal position.

In an exemplary embodiment, the support arm is resiliently coupled to the case. The resilient force member may be configured to impact a surface of the case, e.g. a front case or a rear case, to generate the audible signal.

In an exemplary embodiment, the support arm extends substantially in parallel with a longitudinal axis of the drug delivery device.

In an exemplary embodiment, the resilient force member, in particular its center or first end is coupled, in particular clamped, to the case.

In an exemplary embodiment, when a proximal end of the plunger passes the support arm in the distal direction, the support arm is free to relax radially inwards, thus pulling the legs of the resilient force member out of the notch allowing the legs to relax and strike a surface of the case for generating the audible signal.

In another exemplary embodiment, when a proximal end of the plunger passes the support arm in the distal direction, the support arm is free to relax radially inwards thus also displacing the protrusion in the distal direction and releasing the second end of the resilient force member, allowing the resilient force member to relax and strike a surface the case for generating the audible signal.

Some embodiments may provide a slim autoinjector that reduces premature plunger/button release, thus reduces unfinished dosing. Additionally, some embodiments advantageously provide a loud noise to indicate that the autoinjector has dispensed a full dose of medicament.

Further scope of applicability of the present disclosure will become apparent from the detailed description given hereinafter. However, it should be understood that the detailed description and specific examples, while indicating exemplary embodiments of the disclosure, are given by way of illustration only, since various changes and modifications within the spirit and scope of the disclosure will become apparent to those skilled in the art from this detailed description.

BRIEF DESCRIPTION OF THE FIGURES

The present disclosure will become more fully understood from the detailed description given below and the accompanying drawings, which are given by way of illustration only, and do not limit the present disclosure, and wherein.

Corresponding parts are marked with the same reference symbols in all figures.

DETAILED DESCRIPTION

In the present application, when the term "distal section/end" is used, this refers to the section/end of the device, or the sections/ends of the components thereof, which during use of the device is located closest to a medicament delivery site of a patient. Correspondingly, when the term "proximal section/end" is used, this refers to the section/end of the device, or the sections/ends of the components thereof, which during use of the device is pointing away from the medicament delivery site of the patient.

Figure 1:
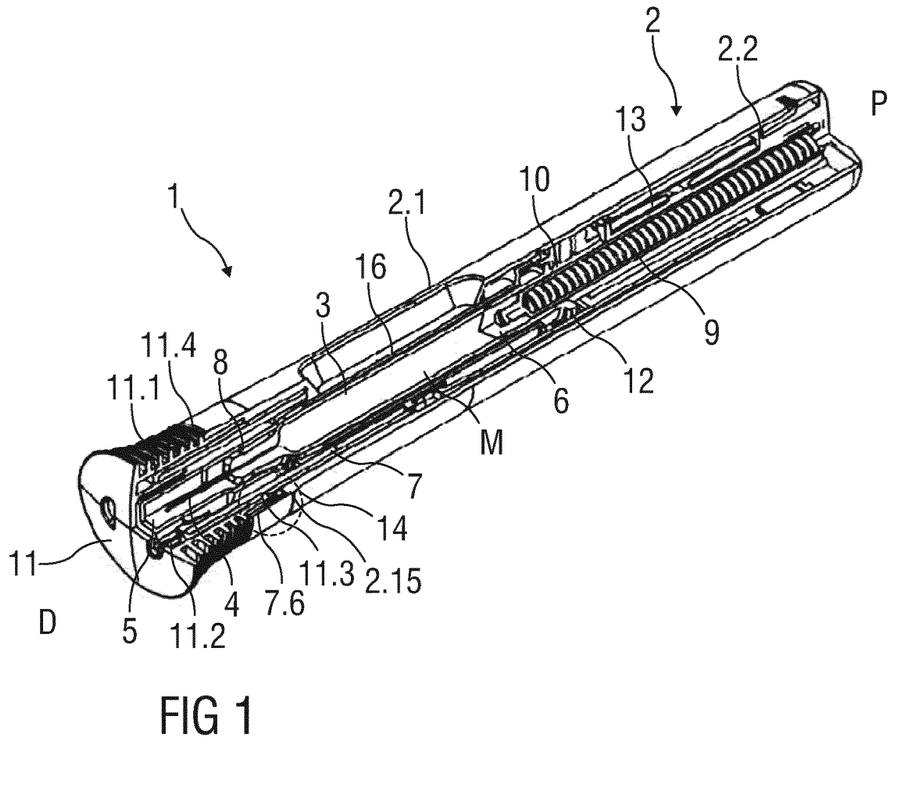
FIG. 1 is a schematic perspective partial section of a drug delivery device comprising an audible indicator.

FIG. 1 shows an exemplary embodiment of a drug delivery device 1, which may be configured as an autoinjector.

In the exemplary embodiment, the drug delivery device 1 comprises a case 2 with a front case 2.1 and a rear case 2.2. The case 2 is adapted to hold a medicament container 3, such as a syringe. (The medicament container is referred to hereinafter as the "syringe 3"). The syringe 3 may be a pre-filled syringe, in particular a 1.0 ml pre-filled syringe, containing a medicament M, and having a needle 4 arranged at a distal end of the syringe 3. In another exemplary embodiment, the medicament container 3 may be a cartridge which includes the medicament M and engages a removable needle (e.g. by threads, snaps, friction, etc.).

The drug delivery device 1 further comprises a protective needle sheath 5 that is coupled to the needle 4. For example, the protective needle sheath 5 is removably coupled to the needle 4. The protective needle sheath 5 may be a rubber needle sheath or a rigid needle sheath, which is composed of rubber and a full or partial plastic shell.

For sealing the syringe 3 proximally and for displacing a medicament M contained in the syringe 3 through the needle 4, a stopper 6 is provided and arranged within the syringe 3.

In the illustrated embodiment, the drug delivery device 1 comprises a needle shroud 7 that is telescopically coupled to the case 2 and movable between a first extended position relative to the case 2 in which the needle 4 is covered and a retracted position relative to the case 2 in which the needle 4 is exposed. Furthermore, a shroud spring 8 is arranged to bias the needle shroud 7 distally against the case 2.

Furthermore, a drive spring 9 is arranged within the case 2. A plunger 10 serves for forwarding a force of the drive spring 9 to the stopper 6. The plunger 10 may be hollow, wherein the drive spring 9 is arranged within the plunger 10 biasing the plunger 10 distally against the case 2. In another exemplary embodiment, the plunger 10 may be solid and the drive 9 may engage a proximal end of the plunger 10. In the illustrated embodiment, the drive spring 9 is wrapped around an outer diameter of the plunger 10 and extends within the syringe 3.

Additionally, the drug delivery device 1 comprises a cap 11 that may be removably disposed at a distal end of the case 2, in particular at a distal end of the front case 2.1. The cap 11 may comprise grip features 11.1 for facilitating a removal of the cap 11, e.g., by twisting and/or pulling the cap 11 off the case 2. The cap 11 may further include a grip element 11.2, e.g. a barb, a hook, a narrowed section, etc., arranged to engage the protective needle sheath 5, the case 2 and/or the needle shroud 7.

In the illustrated embodiment, a plunger release mechanism 12 is arranged for preventing release of the plunger 10 prior to retraction of the needle shroud 7 relative to the case 2 and for releasing the plunger 10 once the needle shroud 7 is sufficiently retracted.

Furthermore, a shroud lock mechanism 14 is arranged to prevent retraction of the needle shroud 7 relative to the case 2 when the cap 11 is in place, thereby avoiding unintentional activation of the drug delivery device 1, e.g., if dropped, during shipping or packaging, etc. The shroud lock mechanism 14 may comprise one or more compliant beams 11.3 on the cap 11 and a respective number of apertures 7.6 in the needle shroud 7 adapted to receive each of the compliant beams 11.3.

When the cap 11 is attached to the drug delivery device 1, the compliant beams 11.3 abut a radial stop 2.15 on the case 2, which prevents the compliant beams 11.3 from disengaging the apertures 7.6. Furthermore, when the cap 11 is attached to the drug delivery device 1, an axial proximal movement of the cap 11 relative to the case 2 is limited by a rib 11.4 on the cap 11 that abuts the case 2.

When the cap 11 is pulled off the case 2 distally, the compliant beams 11.3 may abut an edge of the aperture 7.6 and deflect to disengage the aperture 7.6, allowing for removal of the cap 11 and the protective needle sheath 5 attached thereto. In an exemplary embodiment, the compliant beams 11.3 and/or the apertures 7.6 may be ramped to reduce force necessary to disengage the compliant beams 11.3 from the apertures 7.6.

The drug delivery device 1 further comprises an audible indicator 13 for producing an audible feedback for a user or patient indicating completion of medicament delivery. In other words, the audible indicator 13 is provided to indicate to a user or a patient that the full dose of medicament M was spent.

The drug delivery device 1 further may comprise a carrier 16 to allow an accurate support of the syringe 3 during and after an assembling process. The carrier 16 is adapted to mount, position, and hold the syringe 3 within the case 2.

Figure 2:
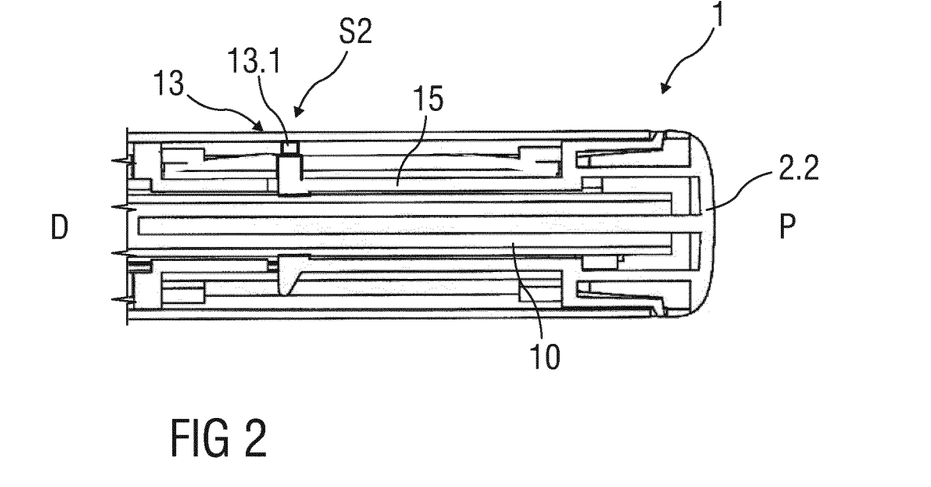
FIG. 2 is a schematic view of a proximal end of the drug delivery device with an exemplary first embodiment of an audible indicator prior to medicament delivery.
Figure 3:
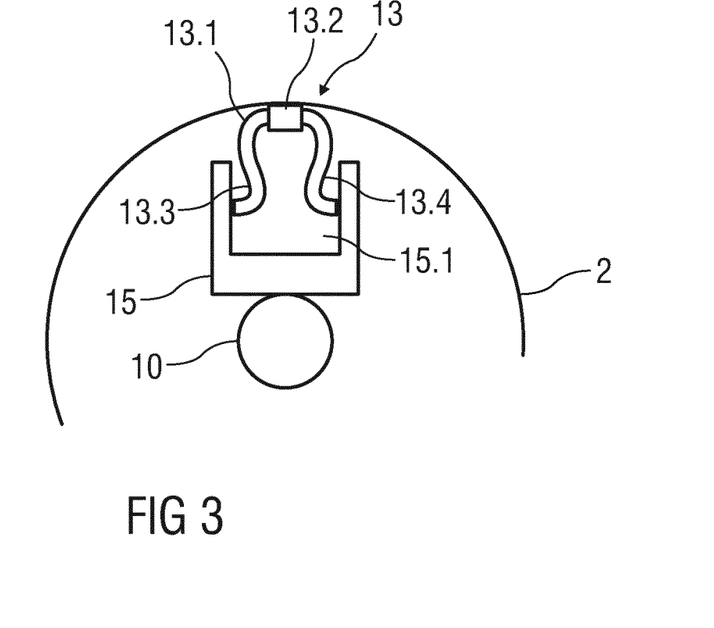
FIG. 3 is a schematic view of the first exemplary embodiment of the audible indicator.

FIG. 2 is a schematic view of a proximal end of the drug delivery device with an exemplary first embodiment of an audible indicator 13. FIG. 3 is a schematic view of the first embodiment of the audible indicator 13.

The audible indicator 13 comprises a resilient force member 13.1 that is configured as a spring comprising a resilient material, e.g. spring steel or spring plastic. Thus, the resilient force member 13.1 is capable of residing in two states. That is, the resilient force member 13.1 may assume two different conformations, one of them stable with limited or no application of an external force and the other one unstable. For example, these two states can include a first or relaxed state S1 (or pre-assembly state, or triggered state), in which the resilient force member 13.1 has a first conformation. In a second or biased state S2 (or primed state), the resilient force member 13.1 can have a second conformation. In FIG. 2, the resilient force member 13.1 is in the biased state S2 and the drug delivery device 1 is in a primed state prior to use, wherein the plunger 10 is in a proximal position. The resilient force member 13.1 may comprise a center 13.2 and two legs 13.3, 13.4 such that the resilient force member 13.1 assumes an Ω-shaped cross section in the biased state S2 as shown in FIG. 3. In other embodiments, the resilient force member 13.1 may comprise a U-shaped or horseshoe-shaped cross section.

The audible indicator 13 furthermore comprises one or more movable support arms 15 which may extend in parallel with a longitudinal axis of the drug delivery device 1 and which may be adapted to radially inwardly abut the plunger 10 when the plunger 10 is in the proximal position. The support arm 15 may have a C-shaped cross section thus defining a retainer in the shape of a notch 15.1 in which the legs 13.3, 13.4 of the resilient force member 13.1 may be received when in the biased state S2 as in FIG. 3. The support arm 15 may be resiliently coupled to the case 2, e.g. the rear case 2.2 or the front case 2.1. The resilient force member 13.1, in particular its center 13.2 may be coupled, in particular clamped, to the case 2, in particular to the front case 2.1 or to the rear case 2.2.

The support arm 15 is biased radially outwards by an outer circumference of the plunger 10. According to the present embodiment, the rear case 2.2 comprises two support arms 15. Alternatively, the rear case 2.2 may comprise only one or more than two support arms 15. In embodiments with more than one resilient force member 13.1, each support arm 15 may be arranged to support one respective resilient force member 13.1.

Figure 4:
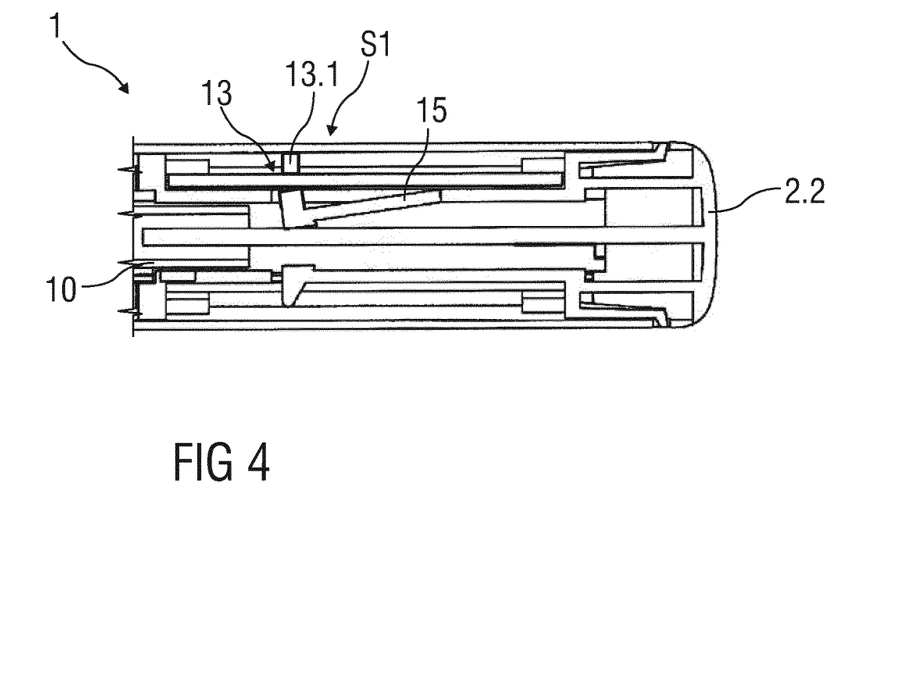
FIG. 4 is a schematic longitudinal section of the proximal part of the drug delivery device after medicament delivery.

For delivering a medicament M into an injection site, the plunger 10 has to be moved distally from the proximal position to a distal position as illustrated in FIG. 4. During medicament delivery, i.e. as long as the plunger 10 has not yet arrived in the distal position, the resilient force member 13.1 is still held within the retainer, i.e. the notch 15.1 of the support arm 15 and therefore remains in the biased state S2.

At the end of medicament delivery, when a proximal end of the plunger 10 passes the support arm 15 in the distal direction D, the support arm 15 is free to relax radially inwards. As the resilient force member 13.1 is coupled to the case 2, radial inward movement of the support arm 15 pulls the legs 13.3, 13.4 of the resilient force member 13.1 out of the retainer, i.e. the notch 15.1 so the legs 13.3, 13.4 relax and move away from each other and strike the case 2, e.g. the front case 2.1 or the rear case 2.2 thereby generating a recognizable audible signal.

FIG. 4 shows a schematic longitudinal section of the proximal part of the drug delivery device 1, wherein the resilient force member 13.1 is in the relaxed state S1 after medicament delivery.

Figure 5:
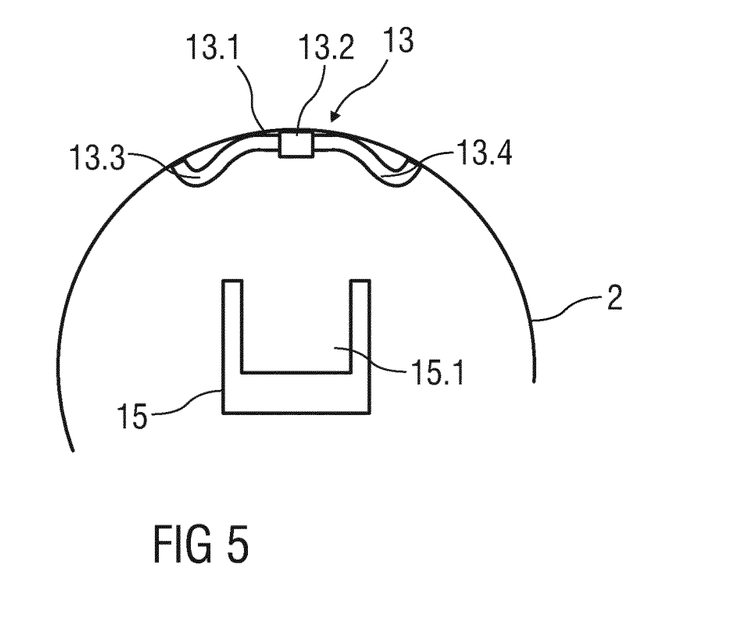
FIG. 5 is a schematic cross section of the audible indicator after medicament delivery.

FIG. 5 shows a schematic cross section of the audible indicator 13 with the resilient force member 13.1 in the relaxed state S1 after medicament delivery.

The skilled person readily understands that application of the audible indicator 13 is not limited to auto-injectors 1. Instead, the audible indicator 13 may likewise be applied in a manually operated drug delivery device 1 for indicating that the plunger 10 has been completely moved into the distal position.

Figure 6:
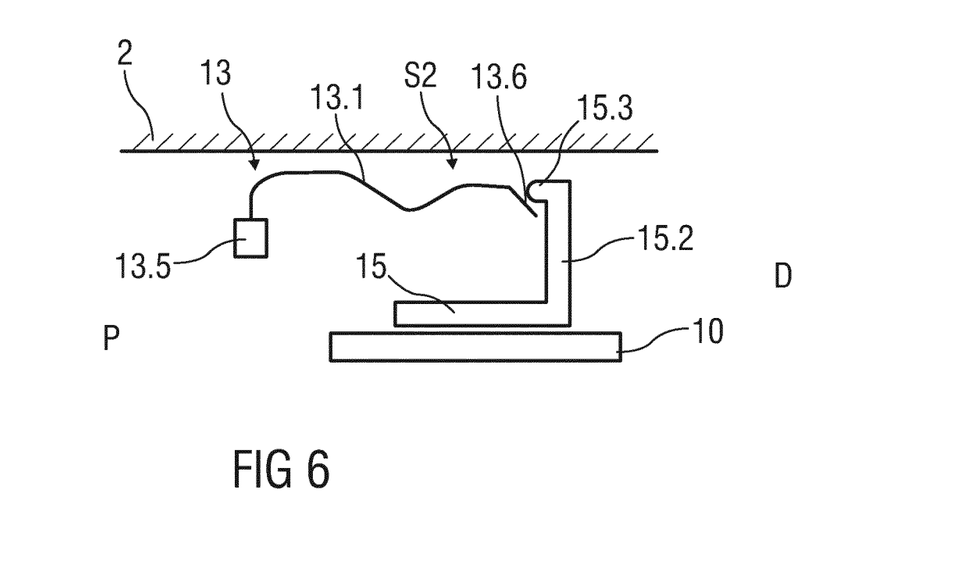
FIGS. 6 and 7 are schematic views of a second exemplary embodiment of an audible indicator.

FIG. 6 is a schematic view of an exemplary second embodiment of an audible indicator 13.

The audible indicator 13 comprises a resilient force member 13.1 that is configured as a spring comprising a resilient material, e.g. spring steel or spring plastic. Thus, the resilient force member 13.1 is capable of residing in two states. That is, the resilient force member 13.1 may assume two different conformations, one of them stable with limited or no application of an external force and the other one unstable. For example, these two states can include a first or relaxed state S1 (or pre-assembly state, or triggered state), in which the resilient force member 13.1 has a first conformation. In a second or biased state S2 (or primed state), the resilient force member 13.1 can have a second conformation. In FIG. 6, the resilient force member 13.1 is in the biased state S2 and the drug delivery device 1 is in a primed state prior to use, wherein the plunger 10 is in a proximal position. The resilient force member 13.1 may be a leaf spring having a first end 13.5 fixed, in particular clamped, to the case 2, in particular to the front case 2.1 or to the rear case 2.2. The resilient force member 13.1 furthermore has a free second end 13.6.

The audible indicator 13 furthermore comprise one or more movable support arms 15 which may extend in parallel with a longitudinal axis of the drug delivery device 1 and which may be adapted to radially inwardly abut the plunger 10 when the plunger 10 is in the proximal position. The support arm 15 may have a radially outwardly directed beam 15.2 having a proximally directed protrusion 15.3 forming a retainer for the second end 13.6 of the resilient force member 13.1 when the resilient force member 13.1 is in the biased state S2 as in FIG. 6. The support arm 15 may be resiliently coupled to the case 2, e.g. the rear case 2.2 or the front case 2.1.

The support arm 15 is biased radially outwards by an outer circumference of the plunger 10. The rear case 2.2 may comprise two support arms 15. Alternatively, the rear case 2.2 may comprise only one or more than two support arms 15. In embodiments with more than one resilient force member 13.1, each support arm 15 may be arranged to support one respective resilient force member 13.1.

Figure 7:
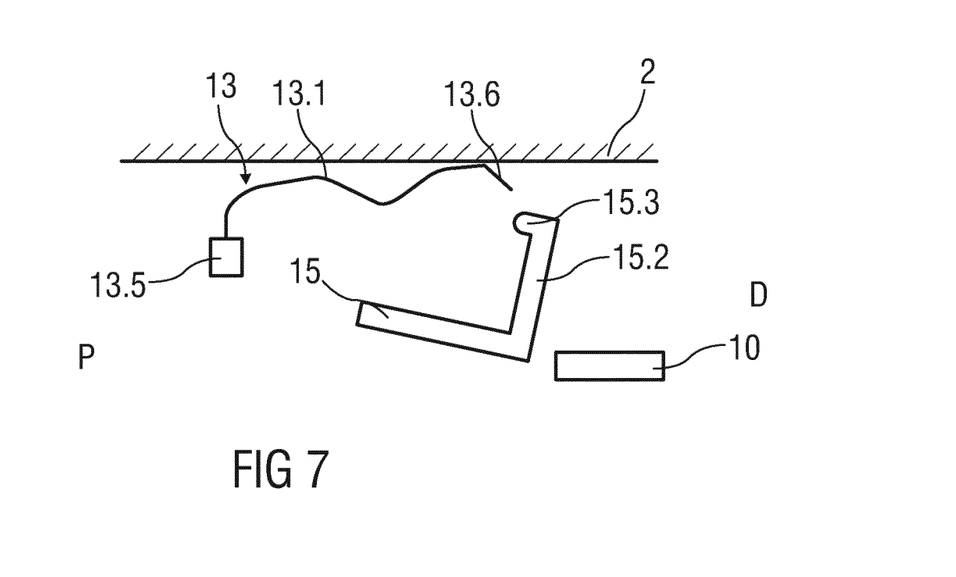

For delivering a medicament M into an injection site, the plunger 10 has to be moved distally from the proximal position to a distal position as illustrated in FIG. 7. During medicament delivery, i.e. as long as the plunger 10 has not yet arrived in the distal position, the second end 13.6 of the resilient force member 13.1 is still held by the retainer, i.e. the protrusion 15.3 of the support arm 15 and therefore remains in the biased state S2.

At the end of medicament delivery, when a proximal end of the plunger 10 passes the support arm 15 in the distal direction D, the support arm 15 is free to relax radially inwards. Due to its resilient coupling to the case 2, radial inward movement of the support arm 15 involves not only linear movement but also rotation thereof such that the retainer, i.e. the protrusion 15.3 is displaced in the distal direction D and releases the second end 13.6 of the resilient force member 13.1, so the resilient force member 13.1 relaxes and the second end 13.6 strikes the case 2, e.g. the front case 2.1 or the rear case 2.2 thereby generating a recognizable audible signal.

The skilled person readily understands that application of the audible indicator 13 is not limited to auto-injectors 1. Instead, the audible indicator 13 may likewise be applied in a manually operated drug delivery device 1 for indicating that the plunger 10 has been completely moved into the distal position.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "drug delivery device" shall encompass any type of device or system configured to dispense a drug into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, micro-needle), inhaler (e.g., nasal or pulmonary), implantable (e.g., coated stent, capsule), or feeding systems for the gastro-intestinal tract. The presently described drugs may be particularly useful with injection devices that include a needle, e.g., a small gauge needle.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance, which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-gamma-glutamyl)-des(B30) human insulin; B29-N-(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin. Exemplary GLP-1, GLP-1 analogues and GLP-1 receptor agonists are, for example: Lixisenatide/AVE0010/ZP10/ Lyxumia, Exenatide/Exendin-4/Byetta/Bydureon/ITCA 650/AC-2993 (a 39 amino acid peptide which is produced by the salivary glands of the Gila monster), Liraglutide/ Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')$_2$ fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')$_2$ fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (additions and/or removals) of various components of the substances, formulations, apparatuses, methods, systems and embodiments described herein may be made without departing from the full scope and spirit of the present disclosure, which encompass such modifications and any and all equivalents thereof.

LIST OF REFERENCES 1 drug delivery device
1.1 drive sub assembly
2 case
2.1 front case
2.2 rear case
2.3 bearing pin
2.4 aperture
2.15 radial stop
3 medicament container, syringe
4 needle
5 protective needle sheath
6 stopper
7 needle shroud
7.6 apertures
8 shroud spring
9 drive spring
10 plunger
11 cap
11.1 grip features
11.2 grip element
11.3 compliant beams
11.4 rib
12 plunger release mechanism
13 audible indicator 13.1 resilient force member
13.2 center
13.3 leg
13.4 leg
13.5 first end
13.6 second end
14 shroud lock mechanism
15.1 notch
15.2 beam
15.3 protrusion
D distal direction
P proximal direction
S1 relaxed state
S2 biased state

The invention claimed is:

1. An audible indicator for use with a drug delivery device, the audible indicator comprising:
   a resilient force member configured to reside in one of a relaxed state and a biased state, and
   a retainer comprising a movable support arm adapted to radially inwardly abut a plunger to maintain the resilient force member in the biased state when the plunger is in a proximal position,
   wherein the resilient force member is configured to release stored energy to impact a surface to generate an audible signal when the resilient force member changes from the biased state into the relaxed state; wherein the resilient force member is configured to disengage from the movable support arm, and wherein the resilient force member is in the relaxed state after disengaging from the movable support arm.

2. The audible indicator according to claim 1, wherein the resilient force member comprises a resilient material.

3. The audible indicator according to claim 1, wherein the resilient force member comprises a center portion and two legs such that the resilient force member assumes an Ω-shaped, U-shaped or horseshoe-shaped cross section in the biased state.

4. The audible indicator according to claim 1, wherein the retainer comprises a notch formed in the support arm, the notch being configured to receive legs of the resilient force member when the resilient force member is in the biased state.

5. The audible indicator according to claim 1, wherein the retainer comprises a radially outwardly directed beam having a protrusion on the support arm, wherein a second end of the resilient force member is retained by the protrusion when the resilient force member is in the biased state.

6. The audible indicator according to claim 1, wherein the resilient force member is a leaf spring having a first end configured to be fixed and a free second end.

7. The indicator device of claim 1, wherein the plunger is translatable in a distal direction relative to the retainer.

8. A drug delivery device, comprising:
   a case,
   a plunger, and
   an audible indicator comprising
      a resilient force member configured to reside in one of a relaxed state and a biased state, and
      a retainer comprising a movable support arm adapted to radially inwardly abut the plunger to maintain the resilient force member in the biased state when the plunger is in a proximal position,
   wherein the resilient force member is configured to release stored energy to impact a surface of the case to generate an audible signal when the resilient force member changes from the biased state into the relaxed state; wherein the resilient force member is configured to disengage from the movable support arm, and wherein the resilient force member is in the relaxed state after disengaging from the movable support arm.

9. The drug delivery device according to claim 8, wherein the resilient force member is configured to change from the biased state into the relaxed state by a movement of the plunger.

10. The drug delivery device according to claim 9, wherein the resilient force member is configured to change from the biased state into the relaxed state by the movement of the plunger towards a distal position at an end of a medicament delivery process.

11. The drug delivery device according to claim 9, wherein a center or first end of the resilient force member is coupled to the case.

12. The drug delivery device according to claim 8, wherein the support arm is resiliently coupled to the case.

13. The drug delivery device according to claim 8, wherein the support arm extends substantially in parallel with a longitudinal axis of the drug delivery device.

14. The drug delivery device according to claim 8, wherein, when a proximal end of the plunger passes the support arm in a distal direction, the support arm is free to relax radially inwards, pulling legs of the resilient force member out of a notch allowing the legs to relax and strike a surface of the case for generating the audible signal.

15. The drug delivery device according to claim 8, wherein, when a proximal end of the plunger passes the support arm in a distal direction, the support arm is free to relax radially inwards, displacing a protrusion in the distal direction and releasing a second end of the resilient force member, allowing the resilient force member to relax and strike a surface the case for generating the audible signal.

16. The drug delivery device of claim 8, wherein the plunger is configured to move in a distal direction relative to the support arm.

17. A method comprising:
   containing legs of an audible indicator in a notch of a support arm extending from a plunger of an autoinjector, wherein the support arm comprises a retainer and is configured to radially inwardly abut the plunger when the plunger is in a proximal position, the support arm arranged such that the support arm and the notch extend along a stem of the plunger, wherein the audible indicator is in a biased position,
   moving the plunger from a proximal position to a distal position, and
   emitting an audible signal by disengaging the legs of the audible indicator from the support arm such that the legs of the audible indicator flex into an unbiased position and contact a case of the autoinjector.

18. The method of claim 17, wherein moving the plunger from a proximal position to a distal position comprises dispensing medicament from a container of the autoinjector.

19. The method of claim 17, wherein the audible signal indicates that a dose of a medicament has been dispensed.

* * * * *

UNITED STATES PATENT AND TRADEMARK OFFICE
CERTIFICATE OF CORRECTION

| | | |
|---|---|---|
| PATENT NO. | : 11,771,838 B2 | Page 1 of 1 |
| APPLICATION NO. | : 16/328251 | |
| DATED | : October 3, 2023 | |
| INVENTOR(S) | : Michael Helmer and Marc Schader | |

It is certified that error appears in the above-identified patent and that said Letters Patent is hereby corrected as shown below:

In the Claims

In Column 11, Line 52, Claim 7, delete "The indicator device" and insert -- The audible indicator --

Signed and Sealed this
Twenty-third Day of January, 2024

*Katherine Kelly Vidal*

Katherine Kelly Vidal
*Director of the United States Patent and Trademark Office*